United States Patent
Kingsley et al.

(10) Patent No.: US 12,161,386 B2
(45) Date of Patent: Dec. 10, 2024

(54) SURGICAL INSTRUMENTS HAVING AN ARTICULATING SECTION SUCH AS FOR USE IN ROBOTIC SURGICAL SYSTEMS

(71) Applicant: Covidien LP, Mansfield, MA (US)

(72) Inventors: Dylan R. Kingsley, Broomfield, CO (US); Crystal A. Adams, Westminster, CO (US); Jason G. Weihe, Longmont, CO (US); William Whitney, Boulder, CO (US); Russell W. Holbrook, Longmont, CO (US); Zachary S. Heiliger, Nederland, CO (US); Curtis M. Siebenaller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 645 days.

(21) Appl. No.: 17/018,346

(22) Filed: Sep. 11, 2020

(65) Prior Publication Data
US 2022/0079661 A1   Mar. 17, 2022

(51) Int. Cl.
*A61B 18/14*    (2006.01)
*A61B 17/00*    (2006.01)
(Continued)

(52) U.S. Cl.
CPC .............. *A61B 18/1445* (2013.01); *A61B 2017/00367* (2013.01); *A61B 2017/00477* (2013.01);
(Continued)

(58) Field of Classification Search
CPC ................ A61B 18/1445; A61B 34/30; A61B 2017/00367; A61B 2017/00526;
(Continued)

(56) References Cited

U.S. PATENT DOCUMENTS 702,472 A    6/1902   Pignolet
2,801,633 A  8/1957   Ehrlich
(Continued)

OTHER PUBLICATIONS

International Search Report and Written Opinion of the International Searching Authority issued in corresponding application PCT/US2021/049805 dated Dec. 23, 2021 (15 pages).
(Continued)

*Primary Examiner* — Tammie K Marlen (57) ABSTRACT

A surgical instrument includes an elongated shaft including an articulating segment. A jaw assembly extends from a distal segment of the elongated shaft. A first jaw member can be actuated between a closed configuration and an open configuration. An articulation cable assembly includes a first articulation cable including a first extending portion, a second extending portion spaced apart from the first extending portion, and a loop portion connecting distal ends of the first and second extending portions of the first articulation cable. A first ferrule is positioned about the loop portion of the first articulation cable. A second articulation cable includes a first extending portion, a second extending portion spaced apart from the first extending portion, and a loop portion connecting distal ends of the first and second extending portions of the second articulation cable. A second ferrule is positioned about the loop portion of the second articulation cable.

20 Claims, 10 Drawing Sheets

(51) Int. Cl.
*A61B 18/00* (2006.01)
*A61B 34/30* (2016.01)

(52) U.S. Cl.
CPC ............. *A61B 2018/00077* (2013.01); *A61B 2018/1455* (2013.01); *A61B 34/30* (2016.02)

(58) Field of Classification Search
CPC ........... A61B 2018/00077; A61B 2018/00083; A61B 34/37
See application file for complete search history.

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| 4,793,218 A | 12/1988 | Jordan et al. | |
| D299,413 S | 1/1989 | DeCarolis | |
| 5,100,506 A | 3/1992 | Sturtevant et al. | |
| 5,242,456 A | 9/1993 | Nash et al. | |
| D343,453 S | 1/1994 | Noda | |
| 5,302,234 A | 4/1994 | Grace et al. | |
| 5,317,938 A | 6/1994 | de Juan, Jr. et al. | |
| D348,930 S | 7/1994 | Olson | |
| D349,341 S | 8/1994 | Lichtman et al. | |
| D354,564 S | 1/1995 | Medema | |
| 5,383,471 A | 1/1995 | Funnell | |
| 5,395,364 A | 3/1995 | Anderhub et al. | |
| D358,887 S | 5/1995 | Feinberg | |
| 5,431,667 A | 7/1995 | Thompson et al. | |
| 5,486,185 A | 1/1996 | Freitas et al. | |
| 5,486,189 A | 1/1996 | Mudry et al. | |
| 5,522,830 A | 6/1996 | Aranyi | |
| 5,522,839 A | 6/1996 | Pilling | |
| 5,539,973 A | 7/1996 | Smith et al. | |
| 5,571,129 A | 11/1996 | Porter | |
| 5,620,447 A | 4/1997 | Smith et al. | |
| 5,626,609 A | 5/1997 | Zvenyatsky et al. | |
| D384,413 S | 9/1997 | Zlock et al. | |
| 5,707,392 A | 1/1998 | Kortenbach | |
| 5,716,374 A | 2/1998 | Francese et al. | |
| 5,752,973 A | 5/1998 | Kieturakis | |
| H1745 H | 8/1998 | Paraschac | |
| 5,792,135 A | 8/1998 | Madhani et al. | |
| 5,833,692 A | 11/1998 | Cesarini et al. | |
| D402,028 S | 12/1998 | Grimm et al. | |
| 5,848,986 A | 12/1998 | Lundquist et al. | |
| D408,018 S | 4/1999 | McNaughton | |
| D416,089 S | 11/1999 | Barton et al. | |
| 6,013,028 A | 1/2000 | Jho et al. | |
| D424,694 S | 5/2000 | Tetzlaff et al. | |
| D425,201 S | 5/2000 | Tetzlaff et al. | |
| 6,117,158 A | 9/2000 | Measamer et al. | |
| H1904 H | 10/2000 | Yates et al. | |
| 6,202,465 B1 | 3/2001 | Jankoski et al. | |
| 6,277,117 B1 | 8/2001 | Tetzlaff et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| 6,817,974 B2 | 11/2004 | Cooper et al. | |
| D502,994 S | 3/2005 | Blake, III | |
| D509,297 S | 9/2005 | Wells | |
| D525,361 S | 7/2006 | Hushka | |
| 7,101,371 B2 | 9/2006 | Dycus et al. | |
| D531,311 S | 10/2006 | Guerra et al. | |
| 7,122,035 B2 | 10/2006 | Canady | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| 7,186,261 B2 | 3/2007 | Prestel | |
| D541,418 S | 4/2007 | Schechter et al. | |
| D541,611 S | 5/2007 | Aglassinge | |
| D541,938 S | 5/2007 | Kerr et al. | |
| D545,432 S | 6/2007 | Watanabe | |
| D547,154 S | 7/2007 | Lee | |
| 7,267,677 B2 | 9/2007 | Johnson et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,799,028 B2 | 9/2010 | Schechter et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,861,906 B2 | 1/2011 | Doll et al. | |
| 7,918,230 B2 | 4/2011 | Whitman et al. | |
| D649,249 S | 11/2011 | Guerra | |
| D649,643 S | 11/2011 | Allen, IV et al. | |
| D661,394 S | 6/2012 | Romero et al. | |
| 8,333,765 B2 | 12/2012 | Johnson et al. | |
| 8,454,602 B2 | 6/2013 | Kerr et al. | |
| 8,523,898 B2 | 9/2013 | Bucciaglia et al. | |
| 8,529,566 B2 | 9/2013 | Kappus et al. | |
| 8,568,408 B2 | 10/2013 | Townsend et al. | |
| 8,579,176 B2 | 11/2013 | Smith et al. | |
| 8,591,510 B2 | 11/2013 | Allen, IV et al. | |
| 8,628,557 B2 | 1/2014 | Collings et al. | |
| 8,679,098 B2 | 3/2014 | Hart | |
| 8,679,140 B2 | 3/2014 | Butcher | |
| 8,685,009 B2 | 4/2014 | Chernov et al. | |
| 8,685,056 B2 | 4/2014 | Evans et al. | |
| 8,696,667 B2 | 4/2014 | Guerra et al. | |
| 8,702,737 B2 | 4/2014 | Chojin et al. | |
| 8,702,749 B2 | 4/2014 | Twomey | |
| 8,745,840 B2 | 6/2014 | Hempstead et al. | |
| 8,747,413 B2 | 6/2014 | Dycus | |
| 8,747,434 B2 | 6/2014 | Larson et al. | |
| 8,752,264 B2 | 6/2014 | Ackley et al. | |
| 8,756,785 B2 | 6/2014 | Allen, IV et al. | |
| 8,845,636 B2 | 9/2014 | Allen, IV et al. | |
| 8,852,185 B2 | 10/2014 | Twomey | |
| 8,864,753 B2 | 10/2014 | Nau, Jr. et al. | |
| 8,864,795 B2 | 10/2014 | Kerr et al. | |
| 8,887,373 B2 | 11/2014 | Brandt et al. | |
| 8,888,771 B2 | 11/2014 | Twomey | |
| 8,900,232 B2 | 12/2014 | Ourada | |
| 8,920,461 B2 | 12/2014 | Unger et al. | |
| 8,939,972 B2 | 1/2015 | Twomey | |
| 8,961,513 B2 | 2/2015 | Allen, IV et al. | |
| 8,961,514 B2 | 2/2015 | Garrison | |
| 8,961,515 B2 | 2/2015 | Twomey et al. | |
| 8,968,283 B2 | 3/2015 | Kharin | |
| 8,968,298 B2 | 3/2015 | Twomey | |
| 8,968,305 B2 | 3/2015 | Dumbauld et al. | |
| 8,968,306 B2 | 3/2015 | Unger | |
| 8,968,307 B2 | 3/2015 | Evans et al. | |
| 8,968,308 B2 | 3/2015 | Horner et al. | |
| 8,968,309 B2 | 3/2015 | Roy et al. | |
| 8,968,310 B2 | 3/2015 | Twomey et al. | |
| 8,968,311 B2 | 3/2015 | Allen, IV et al. | |
| 8,968,317 B2 | 3/2015 | Evans et al. | |
| 8,968,360 B2 | 3/2015 | Garrison et al. | |
| 9,011,435 B2 | 4/2015 | Brandt et al. | |
| 9,023,035 B2 | 5/2015 | Allen, IV et al. | |
| 9,028,492 B2 | 5/2015 | Kerr et al. | |

(56) References Cited

U.S. PATENT DOCUMENTS

| | | | |
|---|---|---|---|
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,055,961 B2 | 6/2015 | Manzo et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 9,192,432 B2 | 11/2015 | Larson et al. |
| 9,259,268 B2 | 2/2016 | Behnke, II et al. |
| 9,265,565 B2 | 2/2016 | Kerr |
| 9,265,568 B2 | 2/2016 | Chernov et al. |
| 9,265,569 B2 | 2/2016 | Hart et al. |
| 9,314,295 B2 | 4/2016 | Garrison |
| 9,375,258 B2 | 6/2016 | Kendrick |
| 9,375,263 B2 | 6/2016 | Allen, IV et al. |
| 9,375,282 B2 | 6/2016 | Nau, Jr. et al. |
| 9,381,059 B2 | 7/2016 | Garrison |
| 9,456,870 B2 | 10/2016 | Chernov et al. |
| 9,474,569 B2 | 10/2016 | Manzo et al. |
| 9,486,220 B2 | 11/2016 | Twomey et al. |
| 9,492,221 B2 | 11/2016 | Garrison |
| 9,615,877 B2 | 4/2017 | Tyrrell et al. |
| 9,636,169 B2 | 5/2017 | Allen, IV et al. |
| 9,668,806 B2 | 6/2017 | Unger et al. |
| 9,693,816 B2 | 7/2017 | Orszulak |
| 9,713,493 B2 | 7/2017 | Waaler et al. |
| 9,820,765 B2 | 11/2017 | Allen, IV et al. |
| 9,844,384 B2 | 12/2017 | Chernov et al. |
| 9,956,030 B2 | 5/2018 | Allen, IV et al. |
| 10,117,705 B2 | 11/2018 | Chernov et al. |
| 10,271,897 B2 | 4/2019 | Allen, IV et al. |
| 10,731,740 B1 | 8/2020 | Cui et al. |
| 2002/0058925 A1 | 5/2002 | Kaplan et al. |
| 2002/0062131 A1 | 5/2002 | Gallo |
| 2002/0099371 A1 | 7/2002 | Schulze et al. |
| 2002/0161364 A1 | 10/2002 | Mulier et al. |
| 2002/0177842 A1 | 11/2002 | Weiss |
| 2003/0060816 A1 | 3/2003 | Iida |
| 2003/0125734 A1 | 7/2003 | Mollenauer |
| 2003/0208186 A1 | 11/2003 | Moreyra |
| 2004/0148992 A1 | 8/2004 | Huang |
| 2004/0193153 A1 | 9/2004 | Sartor et al. |
| 2004/0254573 A1 | 12/2004 | Dycus et al. |
| 2005/0090837 A1 | 4/2005 | Sixto et al. |
| 2005/0240218 A1 | 10/2005 | Freed et al. |
| 2006/0022015 A1 | 2/2006 | Shelton et al. |
| 2006/0025811 A1 | 2/2006 | Shelton |
| 2006/0052777 A1 | 3/2006 | Dumbauld |
| 2006/0161138 A1 | 7/2006 | Orban et al. |
| 2007/0233052 A1 | 10/2007 | Brock |
| 2008/0015631 A1 | 1/2008 | Lee et al. |
| 2008/0083257 A1 | 4/2008 | Taylor et al. |
| 2008/0134812 A1 | 6/2008 | Murata |
| 2008/0264139 A1 | 10/2008 | Rosenbohm et al. |
| 2008/0319442 A1 | 12/2008 | Unger et al. |
| 2008/0319467 A1 | 12/2008 | Wenchell |
| 2009/0088743 A1 | 4/2009 | Masuda |
| 2009/0138006 A1 | 5/2009 | Bales et al. |
| 2009/0182327 A1 | 7/2009 | Unger |
| 2010/0094287 A1 | 4/2010 | Cunningham et al. |
| 2010/0145334 A1 | 6/2010 | Olson et al. |
| 2010/0179540 A1 | 7/2010 | Marczyk et al. |
| 2010/0179545 A1 * | 7/2010 | Twomey ............. A61B 18/1445 606/51 |
| 2010/0274265 A1 | 10/2010 | Wingardner et al. |
| 2010/0292691 A1 | 11/2010 | Brogna |
| 2011/0009864 A1 | 1/2011 | Bucciaglia et al. |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2011/0144665 A1 | 6/2011 | Malkowski |
| 2011/0301600 A1 | 12/2011 | Garrison et al. |
| 2012/0022527 A1 | 1/2012 | Woodruff et al. |
| 2012/0239034 A1 | 9/2012 | Horner et al. |
| 2012/0265241 A1 | 10/2012 | Hart et al. |
| 2012/0296238 A1 | 11/2012 | Chernov et al. |
| 2012/0296371 A1 | 11/2012 | Kappus et al. |
| 2012/0303026 A1 | 11/2012 | Dycus et al. |
| 2012/0330308 A1 | 12/2012 | Joseph |
| 2013/0022495 A1 | 1/2013 | Allen, IV et al. |
| 2013/0071282 A1 | 3/2013 | Fry |
| 2013/0079774 A1 | 3/2013 | Whitney et al. |
| 2013/0123783 A1 | 5/2013 | Marczyk et al. |
| 2013/0274736 A1 | 10/2013 | Garrison |
| 2013/0304066 A1 | 11/2013 | Kerr et al. |
| 2014/0276723 A1 | 9/2014 | Parihar et al. |
| 2017/0042560 A1 | 2/2017 | Lee et al. |
| 2017/0150975 A1 | 6/2017 | Bozung |
| 2017/0265951 A1 | 9/2017 | Grover et al. |
| 2017/0273749 A1 | 9/2017 | Grover et al. |
| 2017/0365923 A1 | 12/2017 | Schmutzler et al. |
| 2018/0028271 A1 | 2/2018 | Rockrohr |
| 2018/0071037 A1 | 3/2018 | Grover et al. |
| 2019/0008600 A1 | 1/2019 | Pedros et al. |
| 2019/0099227 A1 | 4/2019 | Rockrohr |
| 2019/0274769 A1 | 9/2019 | Perdue et al. |
| 2020/0129198 A1 * | 4/2020 | Davison ............. A61B 17/2909 |
| 2020/0179036 A1 | 6/2020 | Honegger et al. |
| 2020/0237453 A1 | 7/2020 | Anglese |
| 2020/0237455 A1 | 7/2020 | Anglese |
| 2020/0246058 A1 | 8/2020 | Traina |
| 2020/0253676 A1 | 8/2020 | Traina |
| 2020/0261166 A1 | 8/2020 | Anglese |
| 2020/0261167 A1 | 8/2020 | Anglese |
| 2020/0261168 A1 | 8/2020 | Anglese |

OTHER PUBLICATIONS

Written Opinion PCT/US2021/049805 dated Mar. 23, 2023; 8 pages.

* cited by examiner

SURGICAL INSTRUMENTS HAVING AN ARTICULATING SECTION SUCH AS FOR USE IN ROBOTIC SURGICAL SYSTEMS

FIELD

The present disclosure relates to surgical instruments and, more specifically, to surgical instruments having an articulating section such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the tissue is severed using a cutting element. Accordingly, electrosurgical forceps are designed to incorporate a cutting element to effectively sever treated tissue. Alternatively, energy-based, e.g., thermal, electrical, ultrasonic, etc., cutting mechanisms may be implemented.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is a surgical instrument including an elongated shaft defining a longitudinal axis, a proximal segment, and a distal segment. The elongated shaft includes an articulating segment between the proximal segment and the distal segment. A jaw assembly extends from the distal segment of the elongated shaft. The jaw assembly includes a first jaw member, and a second jaw member. The first jaw member can be actuated between a closed configuration and an open configuration with respect to the second jaw member. An articulation cable assembly includes a first articulation cable extending along the longitudinal axis of the elongated shaft from the proximal segment to the distal segment. The first articulation cable includes a first extending portion, a second extending portion spaced apart from the first extending portion, and a loop portion connecting distal ends of the first and second extending portions of the first articulation cable. A first ferrule is positioned about the loop portion of the first articulation cable. The first articulation cable is coupled to the distal segment of the elongated shaft. A second articulation cable extends along the longitudinal axis of the elongated shaft from the proximal segment to the distal segment. The second articulation cable includes a first extending portion, a second extending portion spaced apart from the first extending portion, and a loop portion connecting distal ends of the first and second extending portions of the second articulation cable. A second ferrule is positioned about the loop portion of the second articulation cable. The second articulation cable is coupled to the distal segment of the elongated shaft.

In an aspect of the present disclosure, the first jaw member includes a first jaw wire extending proximally therefrom, and the second jaw member includes a second jaw wire extending proximally therefrom.

In an aspect of the present disclosure, a clevis is positioned about the first jaw member and the second jaw member. Distal end portions of the first articulation cable and the second articulation cable are positioned in the clevis. The first ferrule and the second ferrule are positioned in the clevis.

In an aspect of the present disclosure, a skirt is positioned about the articulating segment of the elongated shaft. The skirt includes a first aperture, a second aperture, a third aperture, and a fourth aperture. The first extending portion of the first articulation cable passes through the first aperture. The second extending portion of the first articulation cable passes through the second aperture. The first extending portion of the second articulation cable passes through the third aperture. The second extending portion of the second articulation cable passes through the fourth aperture.

In an aspect of the present disclosure, a jaw cable is coupled to the first jaw member. The jaw cable actuates the first jaw member between the closed configuration and the open configuration. A distal transition plug is positioned about a proximal end portion of the jaw assembly. The distal transition plug maintains positions of the first jaw wire, the second jaw wire, and the jaw cable within the distal segment of the elongated shaft. A proximal transition plug is positioned at an opposite side of the articulating segment from the distal transition plug. The proximal transition plug maintains positions of the second jaw wire, the blade cable, the jaw cable, the first articulation cable, and the second articulation cable within the proximal segment of the elongated shaft. The proximal transition plug allows longitudinal translation of the first and second extending portions of the first articulation cable and the first and second extending portions of the second articulation cable therethrough.

In an aspect of the present disclosure, the jaw assembly includes a blade slidably disposed between the first jaw member and the second jaw member to cut tissue grasped between the first jaw member and the second jaw member. The blade is laterally offset from a center of the first jaw member and the second jaw member.

In an aspect of the present disclosure, a blade cable is coupled to a lateral surface of the blade. The blade cable extends through the distal transition plug.

In an aspect of the present disclosure, a pivot pin extends through proximal arms of the first jaw member and the second jaw member. The pivot pin pivotally couples the first jaw member to the second jaw member.

Provided in accordance with aspects of the present disclosure is a transition plug disposed in the distal segment of the elongated shaft. The transition plug includes an aperture and a slot defined therethrough. The slot is laterally offset from the aperture. A blade rod supports a ferrule at a distal end portion thereof. The blade rod and the ferrule are longitudinally translatable through the aperture of the transition plug. A blade body defines a cutting edge at a distal end portion thereof. The blade body is longitudinally translatable through the slot of the transition plug. The blade body defines a ferrule slot. The ferrule is engaged at least partially within the ferrule slot of the blade body.

In an aspect of the present disclosure, the blade is longitudinally translatable in the jaw assembly along an axis laterally offset from a center of the jaw assembly. The blade body is longitudinally translatable in a groove formed in the second jaw member. The cutting edge extends above an upper surface of the second jaw member from the blade body.

In an aspect of the present disclosure, the blade rod is formed of nitinol, and the ferrule is formed of stainless steel.

In an aspect of the present disclosure, the ferrule is welded to the lateral surface of the blade body.

In an aspect of the present disclosure, a jaw cable is operably coupled to the first jaw member. The jaw cable actuates the first jaw member between the closed configuration and the open configuration. The transition plug defines a second aperture. The jaw cable extends through the second aperture of the transition plug along the longitudinal axis of the elongated shaft.

In an aspect of the present disclosure, the second aperture of the transition plug has a larger diameter than a diameter of the aperture of the transition plug.

BRIEF DESCRIPTION OF THE DRAWINGS

Various aspects and features of the present disclosure are described hereinbelow with reference to the drawings wherein.

DETAILED DESCRIPTION

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Figure 1:
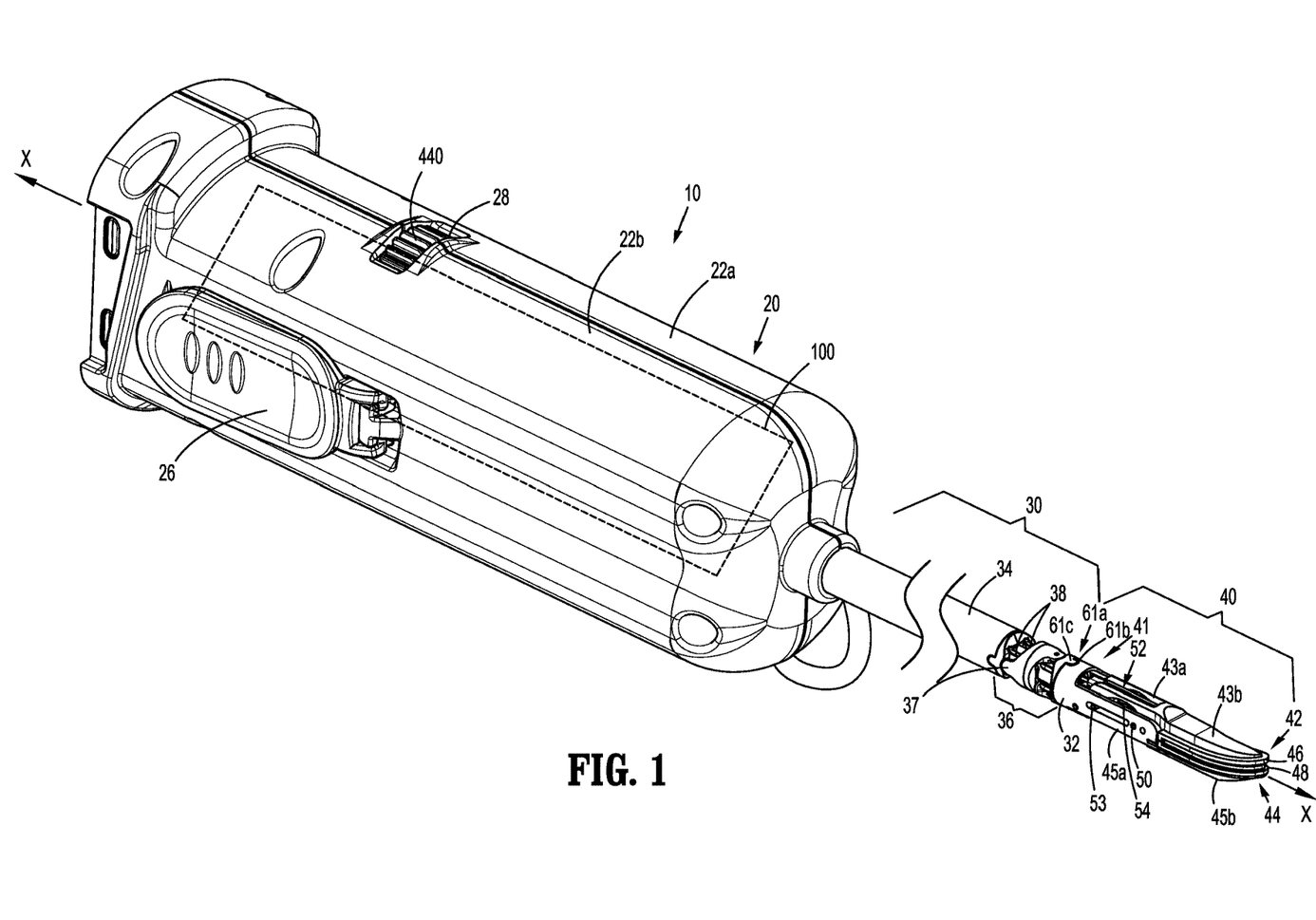
FIG. 1 is a perspective view of a surgical instrument in accordance with the present disclosure configured for mounting on a robotic arm of a robotic surgical system.
Figure 2:
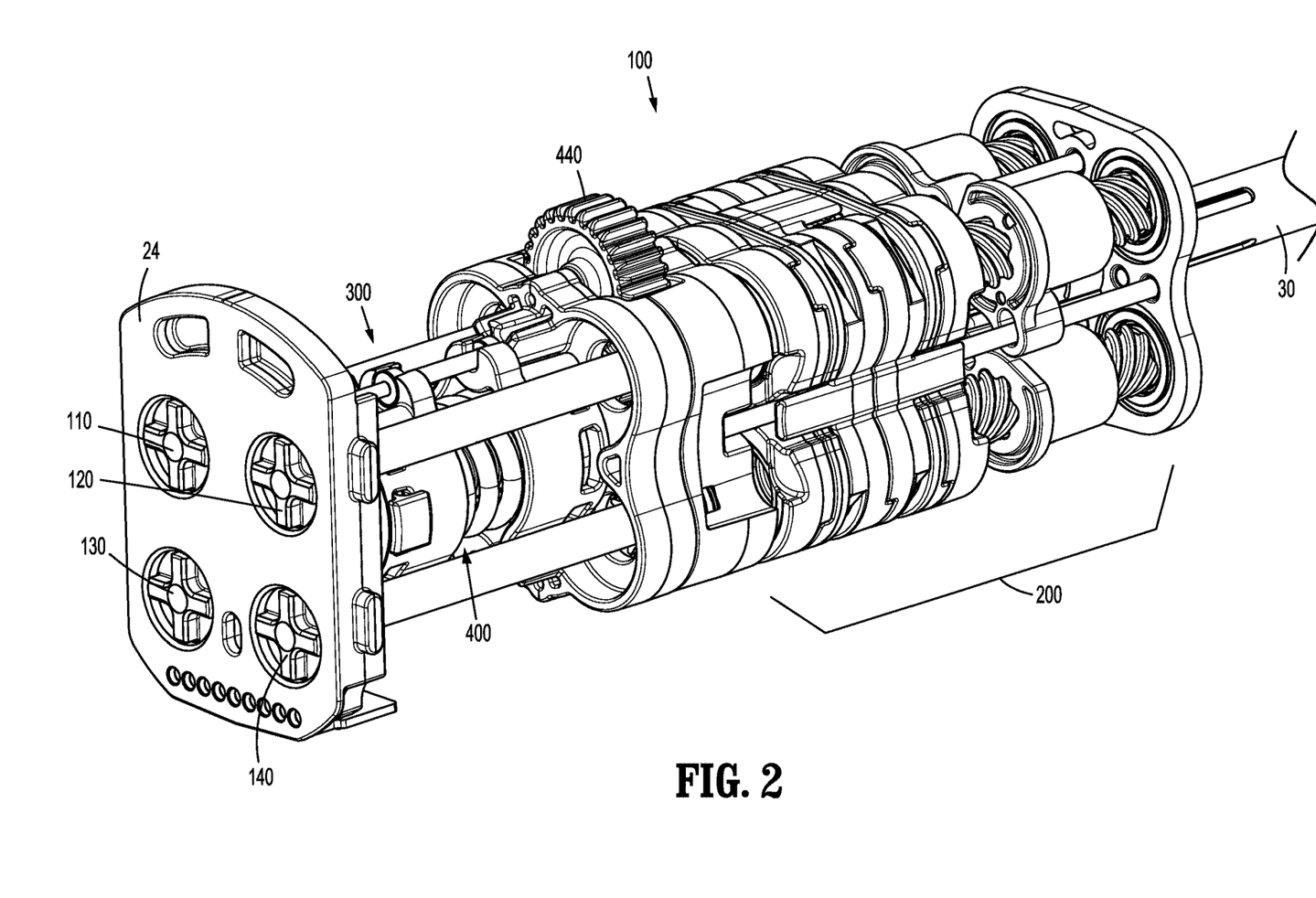
FIG. 2 is a rear perspective view of a proximal portion of the surgical instrument of FIG. 1 with an outer housing removed.
Figure 3:
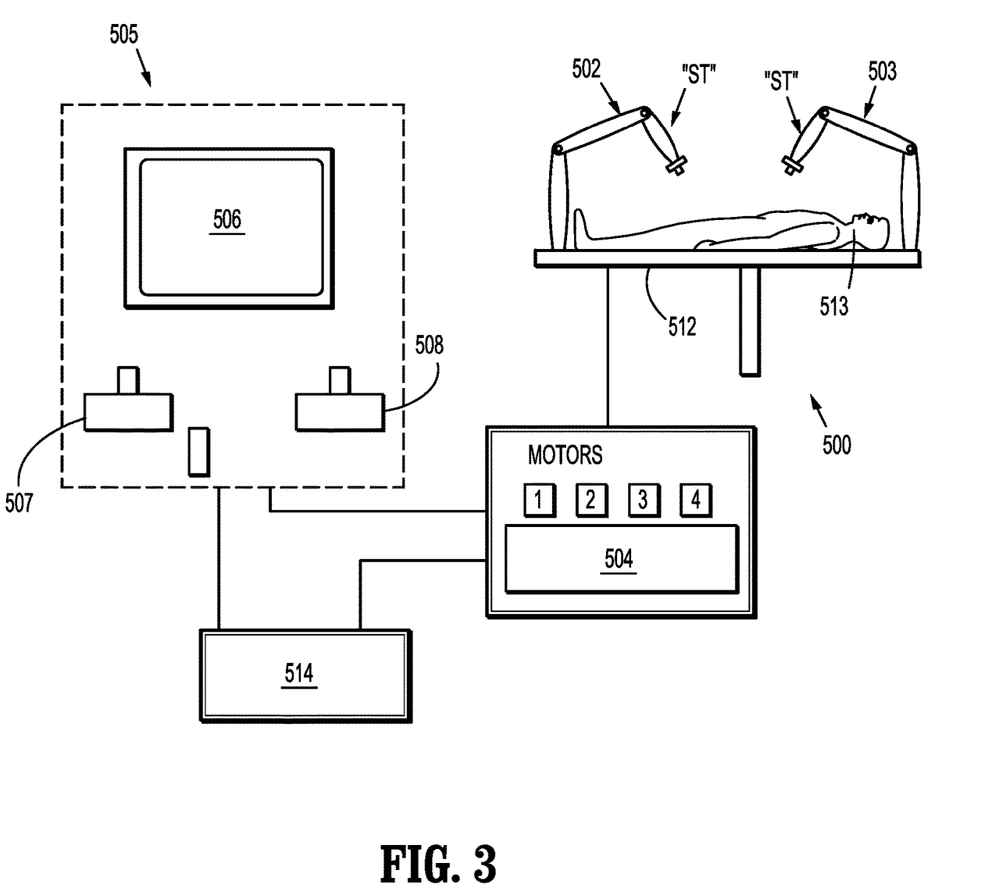
FIG. 3 is a schematic illustration of an exemplary robotic surgical system configured to releasably receive the surgical instrument of FIG. 1.
Figure 4:
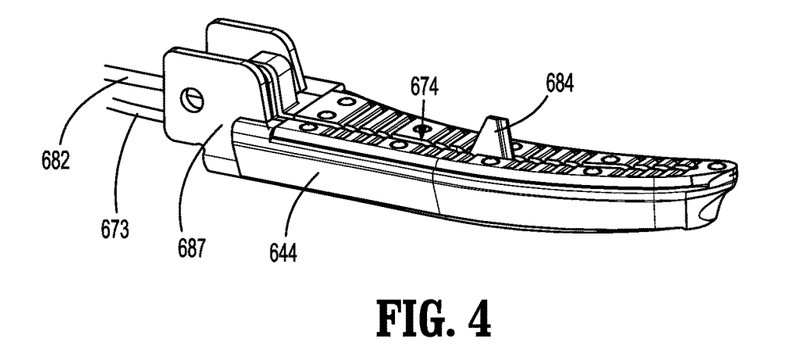
FIG. 4 is a perspective view of a second jaw of a jaw assembly in accordance with the present disclosure.
Figure 5:
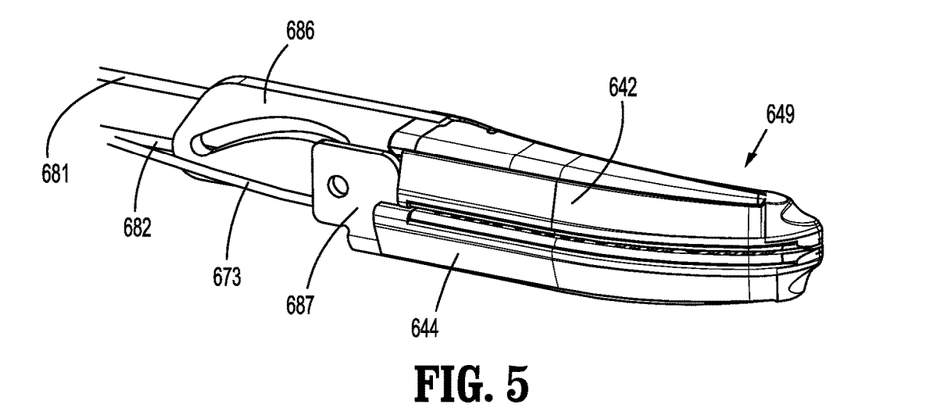
FIG. 5 is a perspective view of the jaw assembly of FIG. 4 showing the first jaw and the second jaw.
Figure 6:
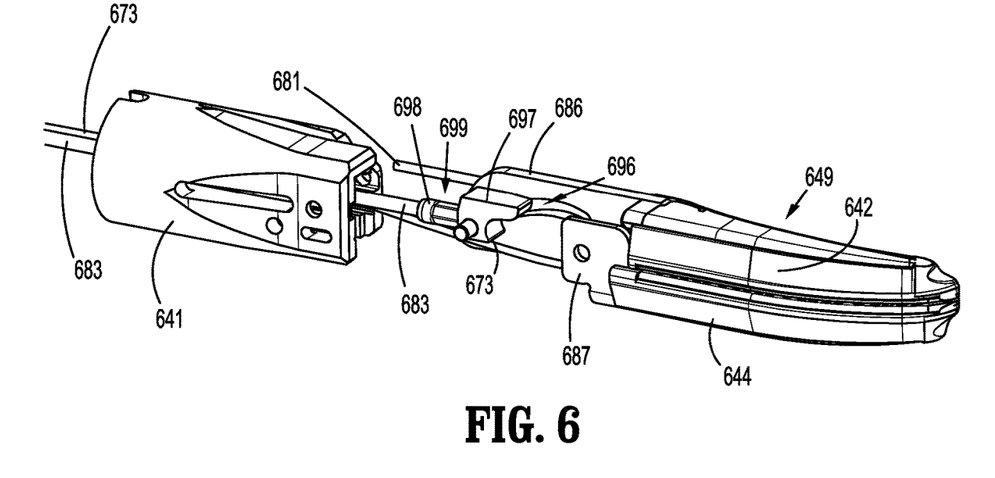
FIG. 6 is a partially exploded, perspective view of the jaw assembly of FIG. 4 showing a cam bar assembly extending through a clevis and coupled to the first jaw.
Figure 7:
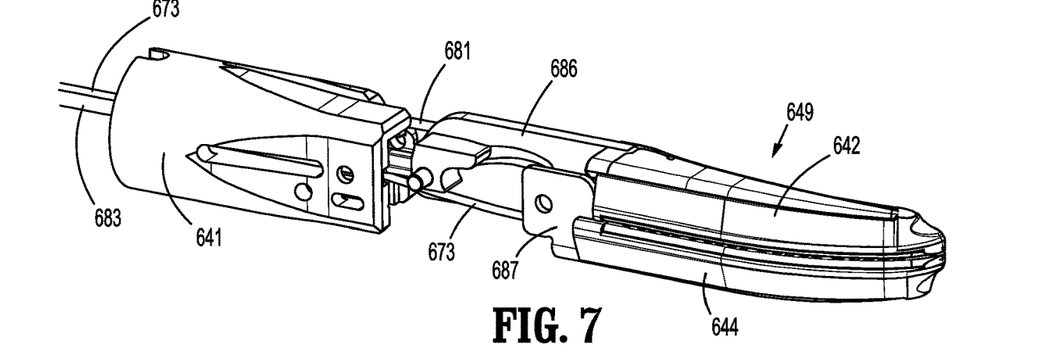
FIG. 7 is a partially exploded, perspective view of the jaw assembly of FIG. 4 showing the clevis advanced toward the jaw assembly.
Figure 8:
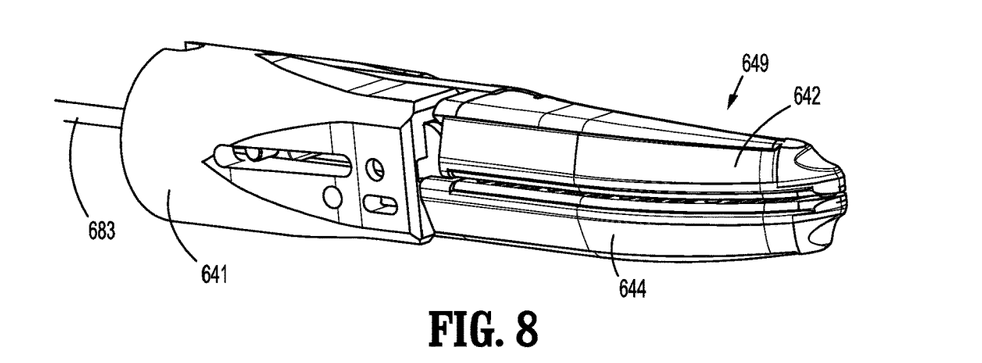
FIG. 8 is a perspective view of the jaw assembly of FIG. 4 showing the clevis positioned about the jaw assembly.
Figure 9:
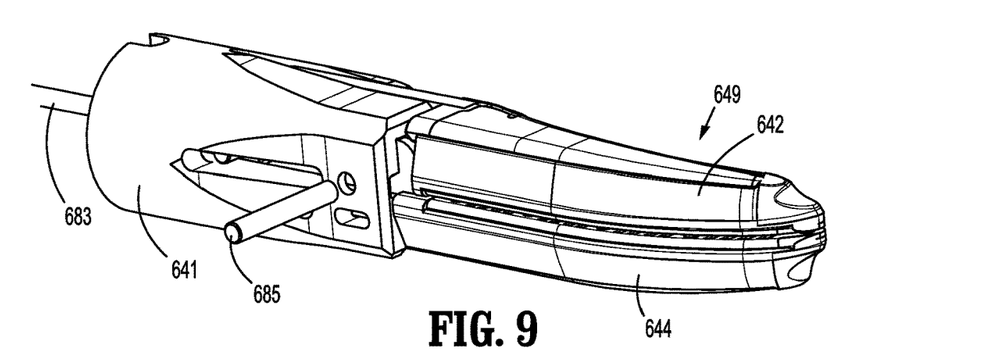
FIG. 9 is a perspective view of the jaw assembly of FIG. 4 with a pivot pin removed from the jaw assembly.
Figure 10:
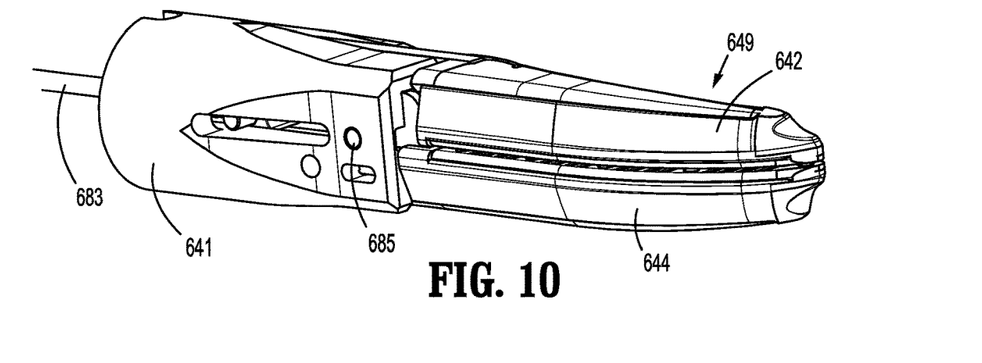
FIG. 10 is a perspective view of the jaw assembly of FIG. 4 with the pivot pin coupled to proximal arms of the first jaw member and the second jaw member.

Referring to FIGS. 1 and 2, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments (including non-robotic surgical instrument) and/or in other suitable surgical systems (including non-robotic surgical systems).

Housing 20 of instrument 10 includes first and second body portion 22a, 22b and a proximal face plate 24 (FIG. 2) that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extends outwardly from opposing sides of housing 20 and enables releasable engagement (directly or indirectly) of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

End effector assembly 40 includes a clevis 41 (extending from, integrally formed with, or constituting distal segment 32 of shaft 30) supporting first and second jaw members 42, 44, respectively. Each jaw member 42, 44 includes a proximal extension portion 43a, 45a and a distal body portion 43b, 45b, respectively. Distal body portions 43b, 45b define opposed tissue-contacting surfaces 46, 48, respectively. Proximal extension portions 43a, 45a are pivotably coupled to one another about a pivot pin 50 and are operably coupled to one another via a cam-slot assembly 52 including a cam pin 53 slidably received within cam slots defined within the proximal extension portion 43a of jaw member 42, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines conductive pathways extending through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48. The electrically conductive pathways to tissue-contacting surfaces 46, 48 of jaw members 42, 44 may be provided by jaw wires extending proximally from jaw members (e.g., such as jaw member 42, 44) described in more detail below with reference to FIGS. 4 to 13.

As noted above, actuation assembly 100 is disposed within housing 20 and includes an articulation assembly 200, cutting drive assembly 300, and jaw drive assembly 400. Articulation assembly 200 is operably coupled between first and second inputs 110, 120, respectively, of actuation assembly 100 and articulation cables 38 (FIG. 1) such that, upon receipt of appropriate rotational inputs into first and/or second inputs 110, 120, articulation assembly 200 manipulates cables 38 (FIG. 1) to articulate end effector assembly 40 in a desired direction, e.g., to pitch and/or yaw end effector assembly 40.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Turning to FIGS. 4 to 10, in some configurations, end effector assembly 40 (FIG. 1) includes a jaw assembly 649 that extends from distal segment 32 of elongated shaft 30 (FIG. 1). The jaw assembly 649 includes a first jaw member 642 and a second jaw member 644. The first jaw member 642 is actuatable between a closed configuration and an open configuration with respect to the second jaw member 644 (e.g., about pivot pin 685). The pivot pin 685 extends through proximal arms 686, 687 of the first jaw member and the second jaw member, respectively. The pivot pin 685 pivotally couples the first jaw member to the second jaw member. A clevis 641 is positioned about the proximal arms 686, 687. The clevis 641 may be substantially the same as the clevis 41 (FIG. 1), unless otherwise indicated.

The first jaw member 642 includes a first jaw wire 681 extending proximally therefrom. The second jaw member 644 includes a second jaw wire 682 extending proximally therefrom. The first jaw wire 681 provides electrosurgical energy to the first jaw member 642, and the second jaw wire 682 provides electrosurgical energy to the second jaw member 644.

The jaw assembly 649 includes a blade 684 (see, e.g., FIG. 4) slidably disposed between the first jaw member 642 and the second jaw member 644 to cut tissue grasped between the first jaw member 642 and the second jaw member 644. The blade 684 is laterally offset from a center axis (see, e.g., axis Y-Y in FIG. 14) of the first jaw member 642 and the second jaw member 644. A blade cable 673 is coupled to the blade 684 and extends proximally therefrom. The blade cable 673 slidably moves the blade 684 through a channel 674 formed in the first jaw member 642. A corresponding channel (not shown) may likewise be defined in the second jaw member 644. The blade cable 673 may be a rod, such as a flexible rod, or a cable such as a braided cable with sufficient stiffness to advance blade 684.

A jaw cable 683 is coupled to and extends proximally from the proximal arm 686 of the first jaw member 642 to actuate the first jaw member 642 between the closed and open configurations. The jaw cable 683 is coupled to the proximal arm 686 by a cam bar assembly 699. Cam bar assembly 699 includes a distal plug 698 coupled to a cam bar 697 disposed in a cam slot 696 of the proximal arm 686.

Referring particularly to FIGS. 1 and 11 to 13, an articulation cable assembly 1131 includes a first articulation cable 1132 and a second articulation cable 1136 extending along the longitudinal axis (e.g., axis X-X of FIG. 1) of the elongated shaft 30 from the proximal segment 34 to the distal segment 32 of the elongated shaft 30. The first articulation cable 1132 has substantially the same configuration as the second articulation cable 1136. The articulation cable assembly 1131 selectively actuates distal segment 32 (and, thus end effector assembly 40) relative to proximal segment 34. Articulation can be achieved about at least two axes of articulation (e.g., yaw and pitch articulation) similarly as described above with respect to articulation cables 38.

Figure 11:
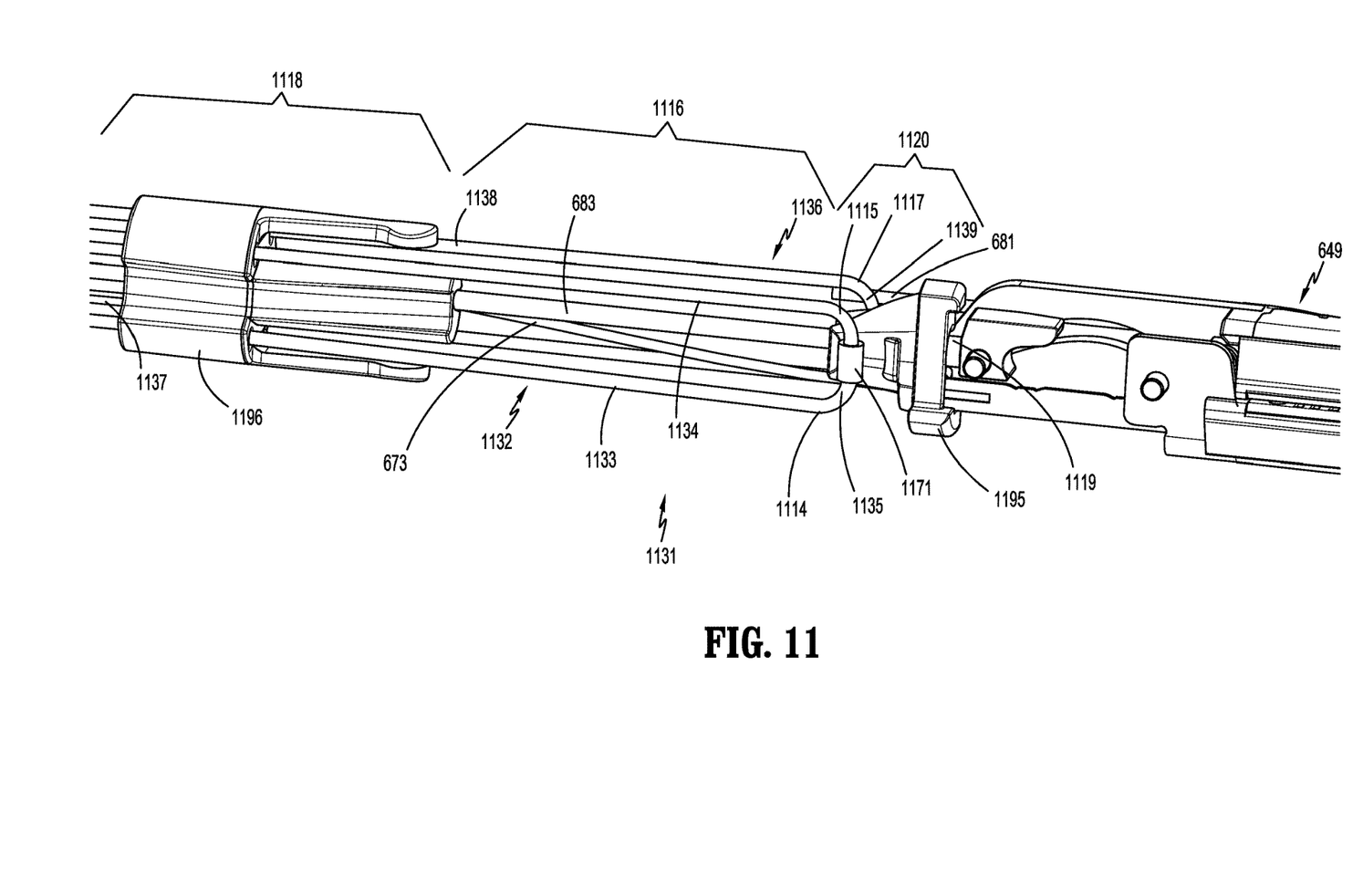
FIG. 11 is a perspective view of an articulation cable assembly in accordance with the present disclosure.
Figure 12:
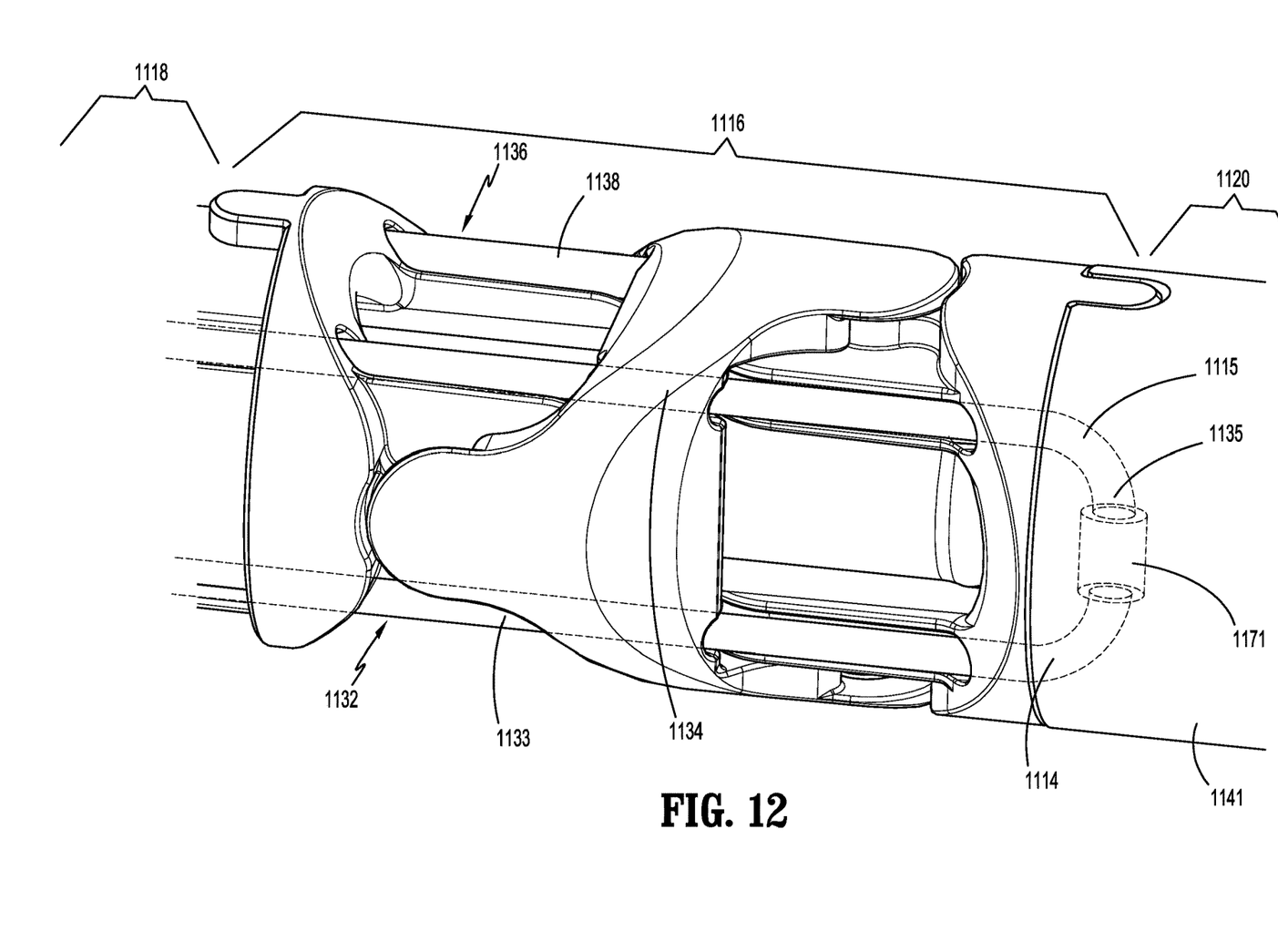
FIG. 12 is an enlarged, perspective view of a portion of the articulation cable assembly of FIG. 11 with an articulation cable shown in phantom and extending through an articulating segment of an elongated shaft, with a distal end portion of the articulation cable including a ferrule secured in a clevis.
Figure 13:
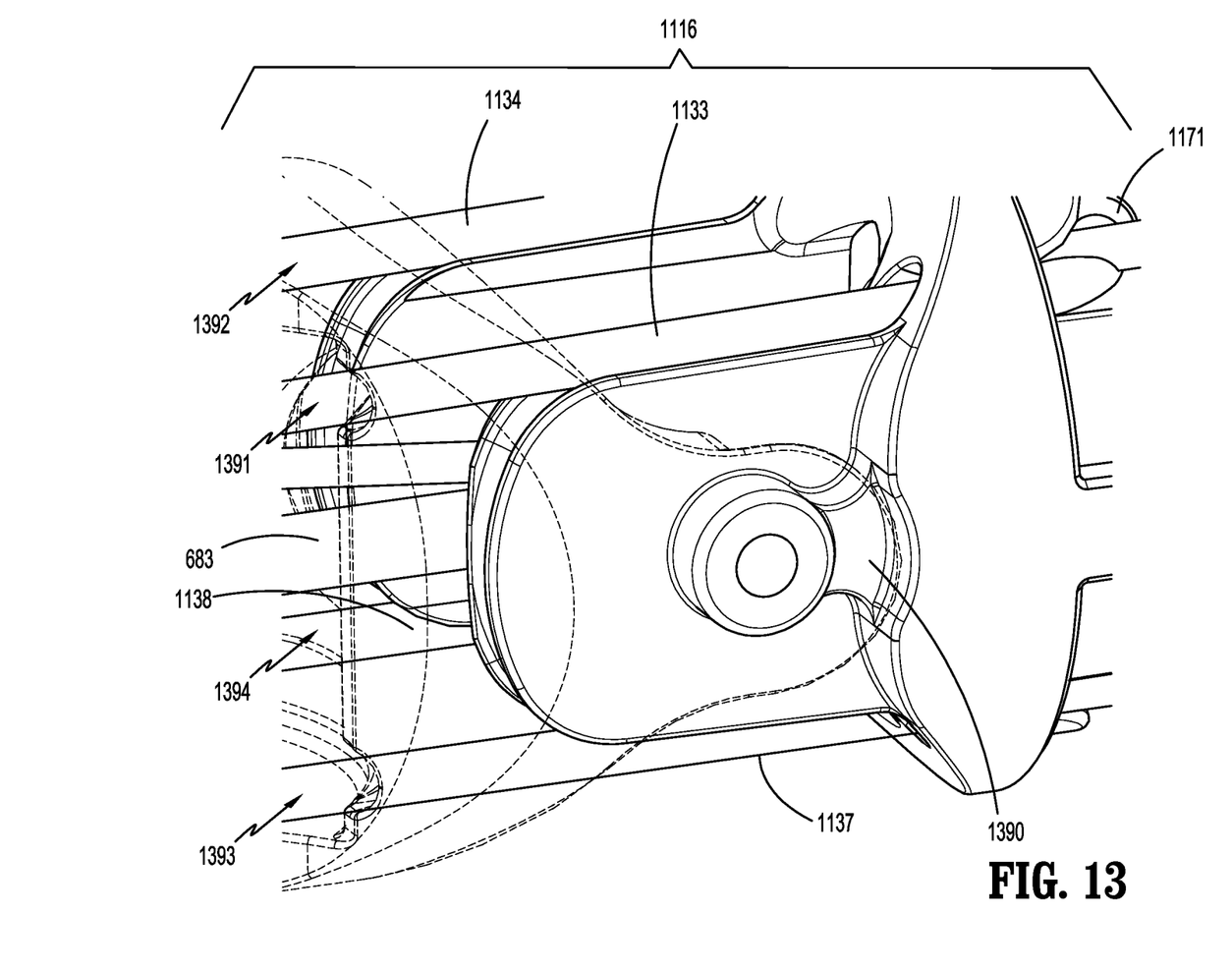
FIG. 13 is a perspective view of a skirt of the articulation cable assembly of FIG. 11.

The first articulation cable 1132 includes a first extending portion 1133, a second extending portion 1134 spaced apart from the first extending portion 1133, and a loop portion 1135 connecting distal ends 1114, 1115, respectively, of the first and second extending portions 1133, 1134 of the first articulation cable 1132. The articulation cable 1132 is a single, integrally formed cable looped around at the distal segment 1120 of the elongated shaft 30 to form the first and second extending portions 1133 and 1134 from a single articulation cable 1132. Using a single articulation cable 1132 to form two strands (i.e., first and second extending portions 1133 and 1134) simplifies manufacturing and reduces manufacturing costs.

The second articulation cable 1136 includes a first extending portion 1137, a second extending portion 1138 spaced apart from the first extending portion 1137, and a loop portion 1139 connecting a distal end (not shown) of the first extending portion 1137 and a distal end 1117 of the second extending portion 1138. The articulation cable 1136 is a single, integrally formed cable looped around at the distal segment 1120 of the elongated shaft 30 to form the first and second extending portions 1137 and 1138 from a single articulation cable 1136. Using a single articulation cable 1136 to form two strands (i.e., first and second extending portions 1137 and 1138) simplifies manufacturing and reduces manufacturing costs.

A first ferrule 1171 is positioned about the loop portion 1135 of the first articulation cable 1132. The first ferrule 1171 is coupled to the distal segment 32 of the elongated shaft 30, thereby coupling the first articulation cable 1132 to the distal segment 32 of the elongated shaft 30. A second ferrule (not shown) is positioned about the loop portion 1139 of the second articulation cable 1136. The second ferrule is substantially the same as the first ferrule 1171, but positioned opposite the first ferrule 1171. The second ferrule, is coupled to the distal segment 32 of the elongated shaft 30, thereby coupling the second cable 1136 to the distal segment 32 of the elongated shaft 30.

The loop portions 1135, 1139 of the first articulation cable 1132 and the second articulation cable 1136 are positioned in the clevis 641. The first ferrule 1171 and the second ferrule are positioned in the clevis 641 and are fixedly secured in the distal segment 20 of the elongated shaft by the clevis 641. The first ferrule 1171 and the second ferrule may each be secured in pockets formed in the distal transition plug 1195, and the clevis 641 may prevent the first ferrule 1171 and the second ferrule from being moved out of the pockets.

A distal transition plug 1195 is positioned about a proximal end portion 1119 of the jaw assembly 649. The distal transition plug 1195 maintains positions of the first jaw wire 681, the second jaw wire 682, and the jaw cable 683 within the distal segment 32 of the elongated shaft 30. A proximal transition plug 1196 is positioned at an opposite side of the articulating segment 36 from the distal transition plug 1195. The proximal transition plug 1196 maintains positions of the second jaw wire 682, the blade cable 673, the jaw cable 683, the first articulation cable 1133, and the second articulation cable 1138 within the proximal segment 34 of the elongated shaft 30. The proximal transition plug 1196 maintains spaced apart positions of the first and second extending portions 1133 and 1134 of the first articulation cable 1132 and the first and second extending portions 1137 and 1138 of the second articulation cable 1136. The proximal transition plug 1196 allows longitudinal translation of the first and second extending portions 1133 and 1134 of the first articulation cable 1132 and the first and second extending portions 1137 and 1138 of the second articulation cable 1136 therethrough. The distal transition plug 1195 maintains two positions for the jaw cable 683, blade rod 1403, and the jaw wire 1482. The first position is for alignment to the required position for jaw function, the second position is for alignment to the required wrist locations. One purpose for the transition plugs 1195, 1196 is to provide a smooth low friction transition between desired positions of cables, wirings, etc. extending therethrough.

The first ferrule 1171 and the second ferrule may be fixedly secured in the distal segment 32 of the elongated shaft 30 between the clevis 641 and the distal transition plug 1195.

Referring particularly to FIG. 13, a skirt 1390 is positioned about the articulating segment 36 of the elongated shaft 30. The skirt 1390 includes a first aperture 1391, a second aperture 1392, a third aperture 1393, and a fourth aperture 1394. The first extending portion 1133 of the first articulation cable 1132 passes through the first aperture 1391. The second extending portion 1134 of the first articulation cable 1132 passes through the second aperture 1392. The first extending portion 1137 of the second articulation cable 1136 passes through the third aperture 1393. The second extending portion 1138 of the second articulation cable 1136 passes through the fourth aperture 1394. The skirt 1390 is positioned to cover the pivot joints between the articulating segment 36 of the elongated shaft 30 and the distal segment 32 of the elongated shaft 30 (an/or in configurations wherein multiple articulating segments 36 are provided, the pivot joints between adjacent articulating segment 36). Thus, pinch points between the articulating segment 36 and the distal segment 32 and/or between articulating segments 36 are eliminated.

Referring particularly to FIGS. 11 and 14 to 17, a transition plug 1485 is disposed in the distal segment 32 of the elongated shaft 30. Transition plug 1485 is substantially the same as transition plug 1195, unless otherwise indicated. The transition plug 1485 includes an aperture 1401 and a slot 1402 defined therethrough. The slot 1402 is laterally offset from the aperture 1401. A blade rod 1403 supports a ferrule 1404 at a distal end portion 1414 thereof. The blade rod 1403 and the ferrule 1404 are longitudinally translatable through the aperture 1401 of the transition plug 1485. A blade body 1403 defines a cutting edge 1484 at a distal end portion 1415 thereof. The blade body 1405 is longitudinally translatable through the slot 1402 of the transition plug 1485. The slot 1402 has a shape corresponding with a shape of the blade body 1405. The slot 1402 maintains a position (e.g., a lateral position) of the blade body 1405 therethrough. The aperture 1401 has a substantially cylindrical shape corresponding with a shape of the ferrule 1404.

The blade body 1405 defines a ferrule slot 1406. The ferrule 1404 is engaged at least partially within the ferrule slot 1404 of the blade body 1405. The ferrule slot 1406 is defined in a lateral surface 1409 of the blade body 1405. The ferrule slot 1406 may extend entirely through a thickness of the blade body 1405, or may be formed as an indent that does not extend entirely through the thickness of the blade body 1405.

The blade body 1405 is longitudinally translatable along an axis (e.g., axis Y-Y of FIG. 14) laterally offset from a center of jaw member 1444. The blade body 1405 is longitudinally translatable in a groove 1474 formed in the second jaw member 1444. The cutting edge 1484 extends above an upper surface 1407 of the second jaw member 1444 from the blade body 1405. The cutting edge 1484 is positioned to cut tissue as it is longitudinally translated. The blade body 1405 has a height that does not extend above the upper surface 1407 of the second jaw member 1444, and thus only the cutting edge 1484 extends above the upper surface 1407 of the second jaw member 1444, although other configurations are also contemplated.

Figure 14:
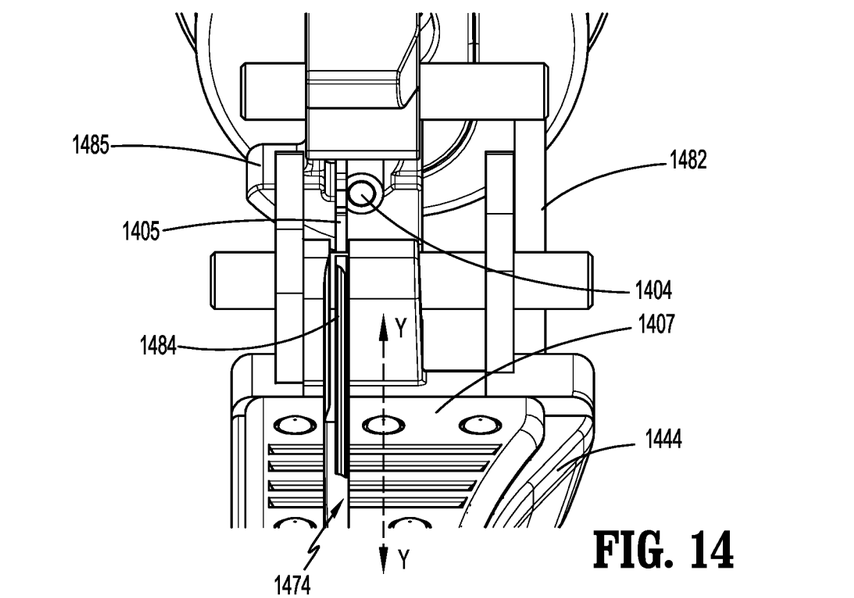
FIG. 14 is a front perspective view of a blade extendable in a jaw assembly in accordance with the present disclosure.
Figure 15:
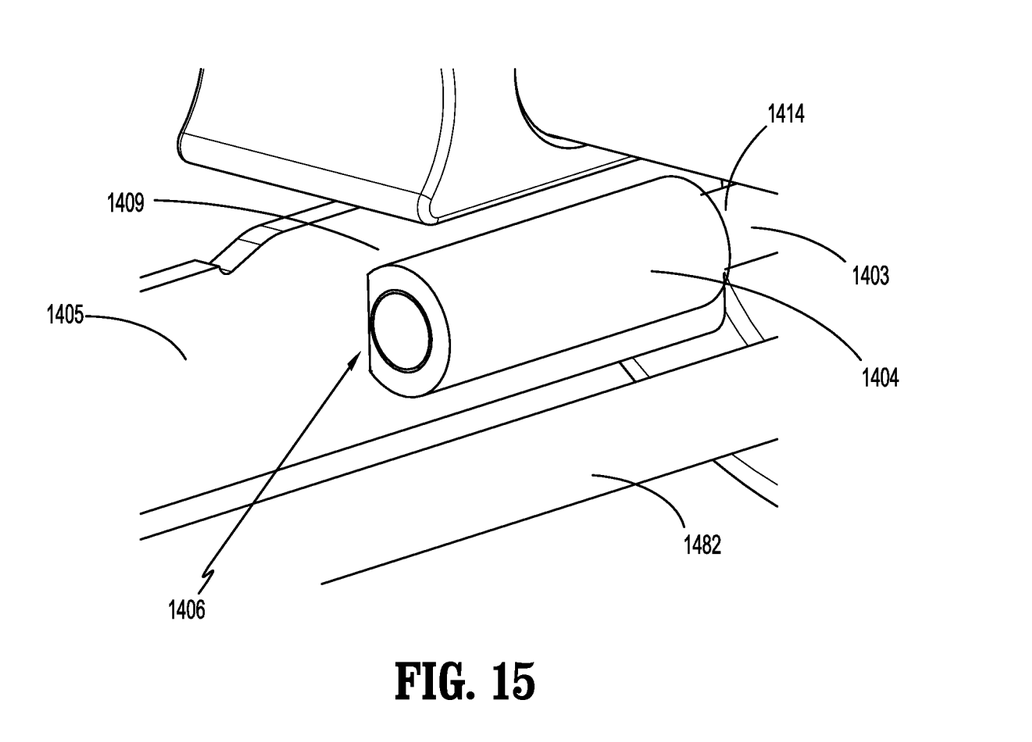
FIG. 15 is a perspective view of a ferrule supported at a distal end portion of a blade rod, the ferrule coupled to a side portion of a blade shaft of the blade of FIG. 14.

As an example, the blade rod 1403 may be formed of or may include nitinol, and the ferrule 1404 may be formed of or may include stainless steel. The ferrule 1404 may be welded to the lateral surface 1409 of the blade body 1405.

Figure 16:
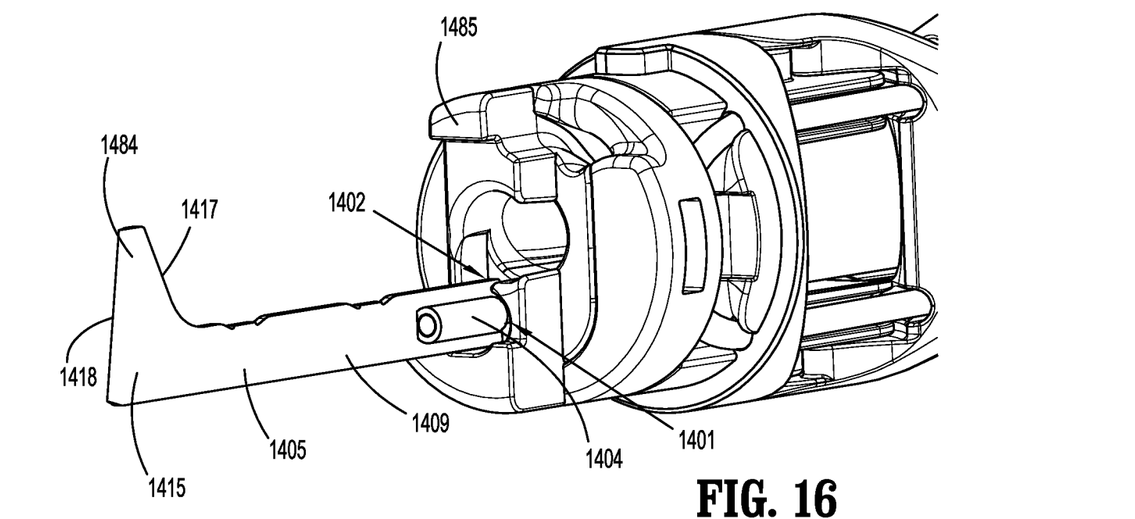
FIG. 16 is a perspective view of the blade rod extended through a slot of a transition plug and the ferrule extended through an aperture of the transition plug of FIG. 14.
Figure 17:
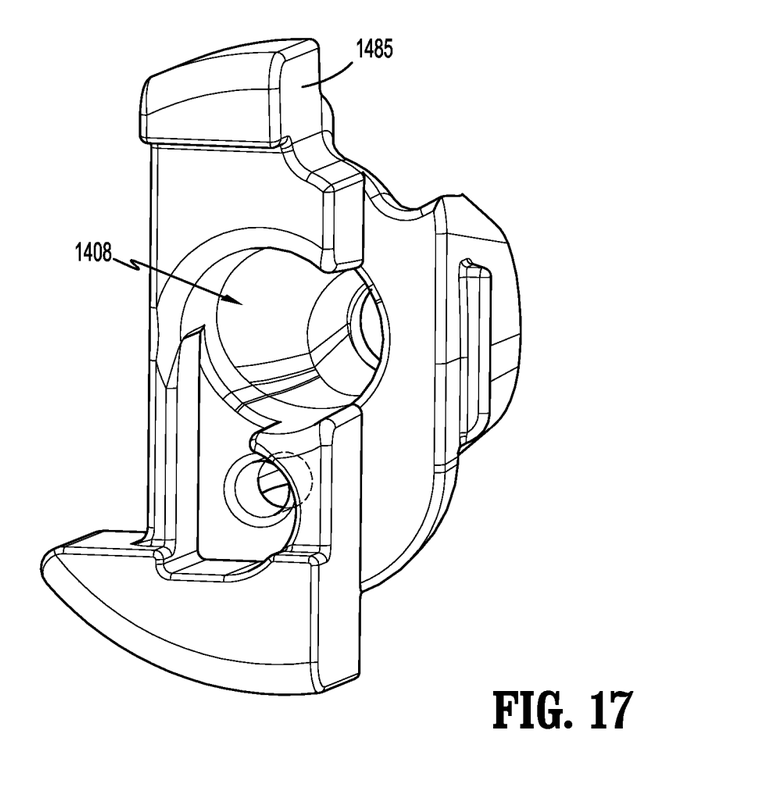
FIG. 17 is a perspective view of the transition plug of FIG. 16 with the blade rod and the ferrule omitted.

A jaw cable (e.g., jaw cable 683 of FIG. 11) extends through a second aperture 1408 of the transition plug 1485 along the longitudinal axis of the elongated shaft 30. The second aperture 1408 may have a substantially cylindrical shape corresponding with a shape of the jaw cable extending therethrough.

The second aperture 1408 of the transition plug 1485 has a larger diameter than a diameter of the aperture 1401 of the transition plug 1485.

Second jaw wire 1482 extends proximally from second jaw member 1444. The second jaw wire 1482 is substantially the same as the second jaw wire 482 described herein.

Cutting edge 1484 may be defined on proximal-facing 1417 and/or distal-facing edges 1418 of the blade body 1405.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. A surgical instrument, comprising:
    an elongated shaft defining a longitudinal axis, a proximal segment, and a distal segment, the elongated shaft including an articulating segment between the proximal segment and the distal segment;
    a jaw assembly extending from the distal segment of the elongated shaft, the jaw assembly including a first jaw member and a second jaw member, the first jaw member configured to be actuated between a closed configuration and an open configuration with respect to the second jaw member;
    a transition component at least partially disposed in the distal segment of the elongated shaft, the transition component including an aperture and a slot defined therethrough, the slot laterally offset from the aperture;
    a blade body configured to cut tissue; and
    a blade rod supporting a ferrule at a distal end portion thereof for attachment of the ferrule to the blade body, the blade rod and the ferrule longitudinally translatable within the aperture of the transition component to translate the blade body through the slot of the transition component.

2. The surgical instrument of claim 1, wherein the blade body is longitudinally translatable in the jaw assembly along an axis laterally offset from a center of the jaw assembly.

3. The surgical instrument of claim 1, wherein the blade body is longitudinally translatable in a groove formed in the second jaw member, and wherein a cutting edge of the blade body extends above an upper surface of the second jaw member from the blade body.

4. The surgical instrument of claim 1, wherein the blade rod is formed of nitinol, and the ferrule is formed of stainless steel.

5. The surgical instrument of claim 1, wherein the ferrule is welded to a side surface of the blade body.

6. The surgical instrument of claim 1, further including a clevis positioned about the jaw assembly and about the transition component.

7. The surgical instrument of claim 1, wherein the first jaw member includes a first jaw wire extending proximally therefrom, and wherein the second jaw member includes a second jaw wire extending proximally therefrom, the first jaw wire configured to provide electrosurgical energy to the first jaw member, and the second jaw wire configured to provide electrosurgical energy to the second jaw member.

8. The surgical instrument of claim 7, further including a jaw cable operably coupled to the first jaw member, the jaw cable configured to actuate the first jaw member between the closed configuration and the open configuration, the transition component defining a second aperture therein, wherein the jaw cable extends through the second aperture of the transition component along the longitudinal axis of the elongated shaft.

9. The surgical instrument of claim 8, wherein the second aperture of the transition component has a larger diameter than a diameter of the aperture of the transition component.

10. The surgical instrument of claim 9, further including a second transition component positioned at an opposite side of the articulating segment from the transition component, the second transition component configured to maintain positions of the second jaw wire, the blade rod, and the jaw cable within the elongated shaft.

11. A surgical instrument, comprising:
an elongated shaft defining a longitudinal axis, a proximal segment, and a distal segment, the elongated shaft including an articulating segment between the proximal segment and the distal segment;
a jaw assembly extending from the distal segment of the elongated shaft, the jaw assembly including a first jaw member and a second jaw member, the first jaw member configured to be actuated between a closed configuration and an open configuration with respect to the second jaw member, the second jaw member defining a groove therein, the groove laterally offset from a central axis of the second jaw member;
a transition component disposed in the distal segment of the elongated shaft, the transition component including an aperture and a slot defined therethrough, the slot laterally offset from the aperture;
a blade body configured to cut tissue; and
a blade rod supporting a ferrule at a distal end portion thereof for attachment of the ferrule to the blade body, the blade rod and the ferrule longitudinally translatable within the aperture of the transition component to translate the blade body through the slot of the transition component, wherein the blade body is longitudinally in the groove of the second jaw member.

12. The surgical instrument of claim 11, further including a ferrule slot defined in a lateral surface of the blade body, the ferrule at least partially secured in the ferrule slot.

13. The surgical instrument of claim 11, wherein a cutting edge of the blade body extends above an upper surface of the second jaw member from the blade body.

14. The surgical instrument of claim 11, wherein the blade rod is formed of nitinol, and the ferrule is formed of stainless steel.

15. The surgical instrument of claim 14, wherein the ferrule is welded to a lateral surface of the blade body.

16. The surgical instrument of claim 11, further including a clevis positioned about the jaw assembly and about the transition component.

17. The surgical instrument of claim 11, wherein the first jaw member includes a first jaw wire extending proximally therefrom, and wherein the second jaw member includes a second jaw wire extending proximally therefrom, the first jaw wire configured to provide electrosurgical energy to the first jaw member, and the second jaw wire configured to provide electrosurgical energy to the second jaw member.

18. The surgical instrument of claim 17, further including a jaw cable operably coupled to the first jaw member, the jaw cable configured to actuate the first jaw member between the closed configuration and the open configuration, the transition component defining a second aperture therein, wherein the jaw cable extends through the second aperture of the transition component along the longitudinal axis of the elongated shaft.

19. The surgical instrument of claim 18, wherein the second aperture of the transition component has a larger diameter than a diameter of the aperture of the transition component.

20. The surgical instrument of claim 19, further including a second transition component positioned at an opposite side of the articulating segment from the transition component, the second transition component configured to maintain positions of the second jaw wire, the blade rod, and the jaw cable within the elongated shaft.

* * * * *